United States Patent
Tebé Poves et al.

(10) Patent No.: US 9,884,133 B2
(45) Date of Patent: Feb. 6, 2018

(54) ELECTRIC DEVICE FOR THE EVAPORATION OF VOLATILE SUBSTANCES

(75) Inventors: Daniel Tebé Poves, Cerdanyola del Vallés (ES); Gianluca Paolazzi, Trento (IT)

(73) Assignee: ZOBELE HOLDING SPA, Trento (IT)

( * ) Notice: Subject to any disclaimer, the term of this patent is extended or adjusted under 35 U.S.C. 154(b) by 1322 days.

(21) Appl. No.: 13/390,369

(22) PCT Filed: Aug. 17, 2009

(86) PCT No.: PCT/EP2009/060624
§ 371 (c)(1),
(2), (4) Date: Apr. 30, 2012

(87) PCT Pub. No.: WO2011/020491
PCT Pub. Date: Feb. 24, 2011

(65) Prior Publication Data
US 2012/0201523 A1    Aug. 9, 2012

(51) Int. Cl.
*A61L 9/03*    (2006.01)
*A61L 9/12*    (2006.01)
*A61L 2/03*    (2006.01)
*A01M 1/20*    (2006.01)

(52) U.S. Cl.
CPC ............. *A61L 2/03* (2013.01); *A01M 1/2077* (2013.01)

(58) Field of Classification Search
USPC .......................... 392/392, 395, 403, 386, 390
See application file for complete search history.

(56) References Cited

U.S. PATENT DOCUMENTS

| | | | |
|---|---|---|---|
| 5,909,845 A | 6/1999 | Greatbatch | |
| 6,285,830 B1 * | 9/2001 | Basaganas Millan | 392/395 |
| 6,580,875 B2 * | 6/2003 | Rymer | 392/395 |
| 7,209,650 B2 * | 4/2007 | Caserta et al. | 392/395 |
| 7,744,833 B2 * | 6/2010 | Varanasi et al. | 422/306 |
| 2005/0213948 A1 | 9/2005 | Caserta | |
| 2008/0226269 A1 * | 9/2008 | DeWitt et al. | 392/386 |

FOREIGN PATENT DOCUMENTS

| | | |
|---|---|---|
| EP | 1064957 A1 | 1/2001 |
| JP | 11075659 A | 3/1999 |
| WO | 0121226 A1 | 3/2001 |
| WO | 0139809 A1 | 6/2001 |

OTHER PUBLICATIONS

International Search Report PCT/EP2009/06024: dated Jan. 29, 2010.

\* cited by examiner

*Primary Examiner* — Dana Ross
*Assistant Examiner* — Lawrence Samuels
(74) *Attorney, Agent, or Firm* — Cantor Colburn LLP

(57) ABSTRACT

The present invention refers to an electric evaporation device with adjustable evaporation intensity, wherein a shield member (4) is displaceable between a minimum evaporation position in which it is interposed between a heating resistor (5) and an upper part of a wick (3), and a maximum evaporation position in which part of the shield member is located below said resistor (5). Since the shield member (4) is moved downwardly below the resistor (5), the upper end (13) of the wick (3) be located very close to an aperture (10) for the exit of the vaporized substance.

10 Claims, 5 Drawing Sheets

ELECTRIC DEVICE FOR THE EVAPORATION OF VOLATILE SUBSTANCES

TECHNICAL FIELD

The present invention refers in general to electric devices for evaporating volatile substances, such as fragrances and/or insecticides.

In more specific terms, the present invention provides an electric evaporation device with adjustable evaporation intensity, in which the undesired condensation of vapor inside the device is prevented.

BRIEF SUMMARY OF RELATED ART

There are many known devices for evaporating volatile substances typically air-fresheners, which include a wick and means for regulating the degree of evaporation of the volatile substance.

An air-freshener of this type is described in the European Patent EP-1031446, in which a movable cap element is used to regulate the degree of evaporation by covering the wick. That cap is a top closed casing which is displaceable above the upper end of the wick, for that part of the vaporized substance reaches and condensates on the inner surface of the cap.

This undesired condensation of product inside the device, contributes to the deterioration of the same and it is unpleasant for the user.

The international publication WO 01/21226 discloses an air-freshener in which the vapor emission rate is controlled by displacing a tubular body above the upper end of the wick, for guiding to some extend the flow of vapor from the wick to the exterior of the device. Since the tubular body is movable above the wick, it is necessary to provide a large volume between the upper part of the wick and the aperture for the exit of vapor to the exterior. This conventional structure implies that the vapor has to flow through a long path until it exist the device, which causes undesired condensation of vapor on the internal surface of the tubular body and other internal surfaces of the device.

Other example of air-freshener incorporating evaporation regulating means, is disclosed in the European Patent EP-1064957. In this case regulation is based on the variation of the chimney effect caused by the ascension of vapor. Since the chimney effect is always produced above the source of heat adjacent to the end of the wick, the regulation means have to be arranged above the wick, which again result in the condensation problems due to the long path that the vapor has to follow. This regulation technique is based on the modification of the geometry of the chimney, which results in apertures appearing in the chimney channel during the regulation through which the vapor escapes, causing the condensation of the vapor on the internal surfaces of the device.

Therefore, it has been detected the need for evaporators which are not affected by the problems associated with the vapor condensation on the interior surfaces of the evaporator.

On the other hand, it is known in the state of the art to provide a protective sleeve element covering the part of the wick extending outside the container of volatile substance. That sleeve element is used to avoid bending of the wick and maintain the correct position of the wick during its use. The U.S. Pat. No. 5,909,845 shows an example of a protected wick of this kind.

BRIEF SUMMARY

An aspect of the invention refers to an electric device for the evaporation of volatile substances, which comprises a container of volatile substances provided with a wick having an upper part protruding from said container, and a lower part inside said container in contact with the volatile substance. The wick is soaked with the volatile substance in liquid state, which raises by capillary action through the wick towards the upper end of the wick.

The device further comprises heating means suitably arranged for heating said upper part of the wick, in order to enhance therefore the evaporation of the liquid immersed in the wick and its diffusion to the surrounding environment.

A shield member is provided in the device for regulating the degree of evaporation of the volatile substance, by interfering or blocking to some extend the heat transfer from the heating means to the wick.

This shield member is displaceable along a direction substantially parallel to the longitudinal axis of the wick, and instead of moving above the wick as it is the case of the devices of the prior art, the shield member is displaceable downwardly below the upper end of the wick, for that it is not necessary to provide a large room above the wick for receiving the regulating means.

The shield member is displaceable between a minimum evaporation position and a maximum evaporation position. In the minimum evaporation position the shield member, or a major part of it, is interposed between said heating means and said upper part of the wick, in such a manner that the heat transfer to the upper part of the wick is effectively reduced and the temperature at the upper part of the wick is minimal.

In the maximum evaporation position, a part of the shield member is located below said heating means, in such a manner that a major part of the heating means is directly facing the side surface of the wick without any barrier being interposed in between, for that the temperature at the upper part of the wick is maximum.

Due to this innovative arrangement of the shield member, the upper end of the wick can be located very close to the aperture for the exit of the vapor to the exterior of the device, which has the effect that most of the vapor can exist outside the device, since the path that vapor has to follow to the exit is very short for that the condensation problems inside the device are reduced significantly.

BRIEF DESCRIPTION OF THE DRAWINGS

To supplement the description that is being made and with the object of assisting in a better understanding of the characteristics of the invention, in accordance with a preferred example of practical embodiment thereof, attached as an integral part of said description, is a set of drawings wherein by way of illustration and not restrictively, the following has been represented.

DETAILED DESCRIPTION

Figure 1:
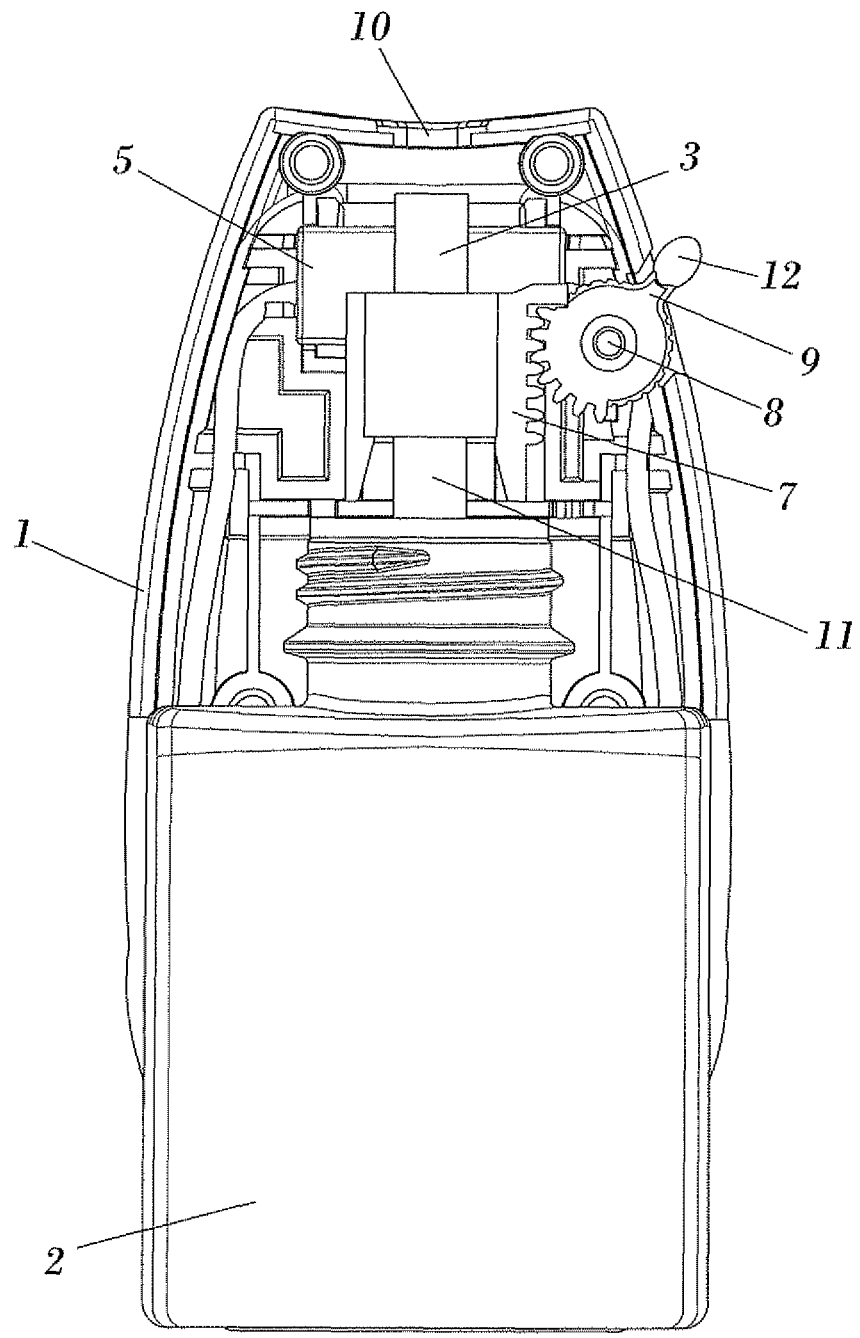
FIG. 1—shows a front elevational view of the device with a part of the casing removed for illustration purposes.

In the preferred embodiment of the invention shown in FIG. 1, the electric device comprises a casing (1) and a container (2) of volatile substances which is detachably engaged with said casing (1). The container (2) in the form of a bottle, is provided with a wick (3) having an upper part (11) extending outside said container (2), and a lower part (not shown) inside the container in contact with a volatile substance.

The wick has the form of a cylindrical rod and during the normal use of the device when it is connected to an electric outlet of a wall, it is vertically arranged so that the part (11) of the wick protruding from the container is at an upper position, and the part of the wick inside the container is at a lower position.

The device includes heating means, for example a heating resistor (5) such as a cemented metal oxide resistor, or any other known type of electric heater suitable for this use.

Preferably, a single heating resistor (5) is provided fixed to the interior surface of the casing (1), adjacent to the upper end (19) of the wick (3) for heating the same. Alternatively, the device comprises more than one heating resistor (5) for heating the upper end of the wick.

Figure 5:
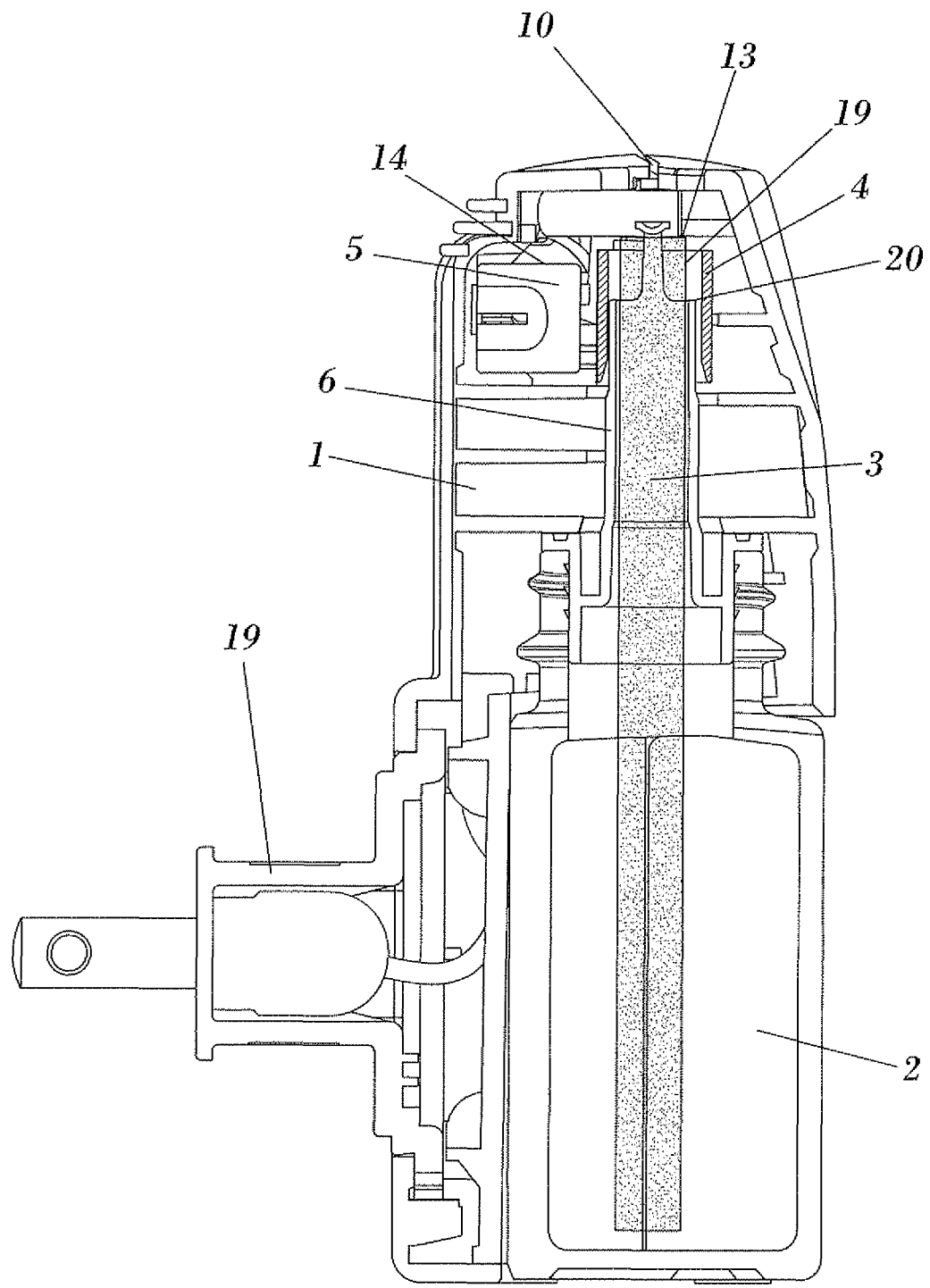
FIG. 5.—shows a sectional side view of the device, in which the regulation means are in the minimum evaporation position.

The casing (1) incorporates an electric plug base (19) for supplying electric power to the resistor (5) and for supporting the device in a wall outlet in the position shown in FIG. 5.

This resistor (5) has the shape of a rectangular prismatic body having a planar upper surface (14) located at a lower level than the top base (13) of the wick (3) during the normal use of the device. Said planar upper surface (14) is substantially orthogonal to the axis of the wick, when the container is coupled with the casing.

A large side surface (15) of the resistor (5) is facing the side surface (16) of the wick (3) and it is substantially parallel to the axis of the wick (3).

Alternatively, the heating resistor (5) is shaped as toroid and it is arranged around the wick.

The device further comprises a shield member (4) which is interposed between the heating means and the wick to act as a barrier for the transfer of heat from the heating means to the wick. This shield member is displaceable so as to block the heat transfer in a lesser or greater extend for regulating the degree of evaporation of the volatile substance.

Figure 2:
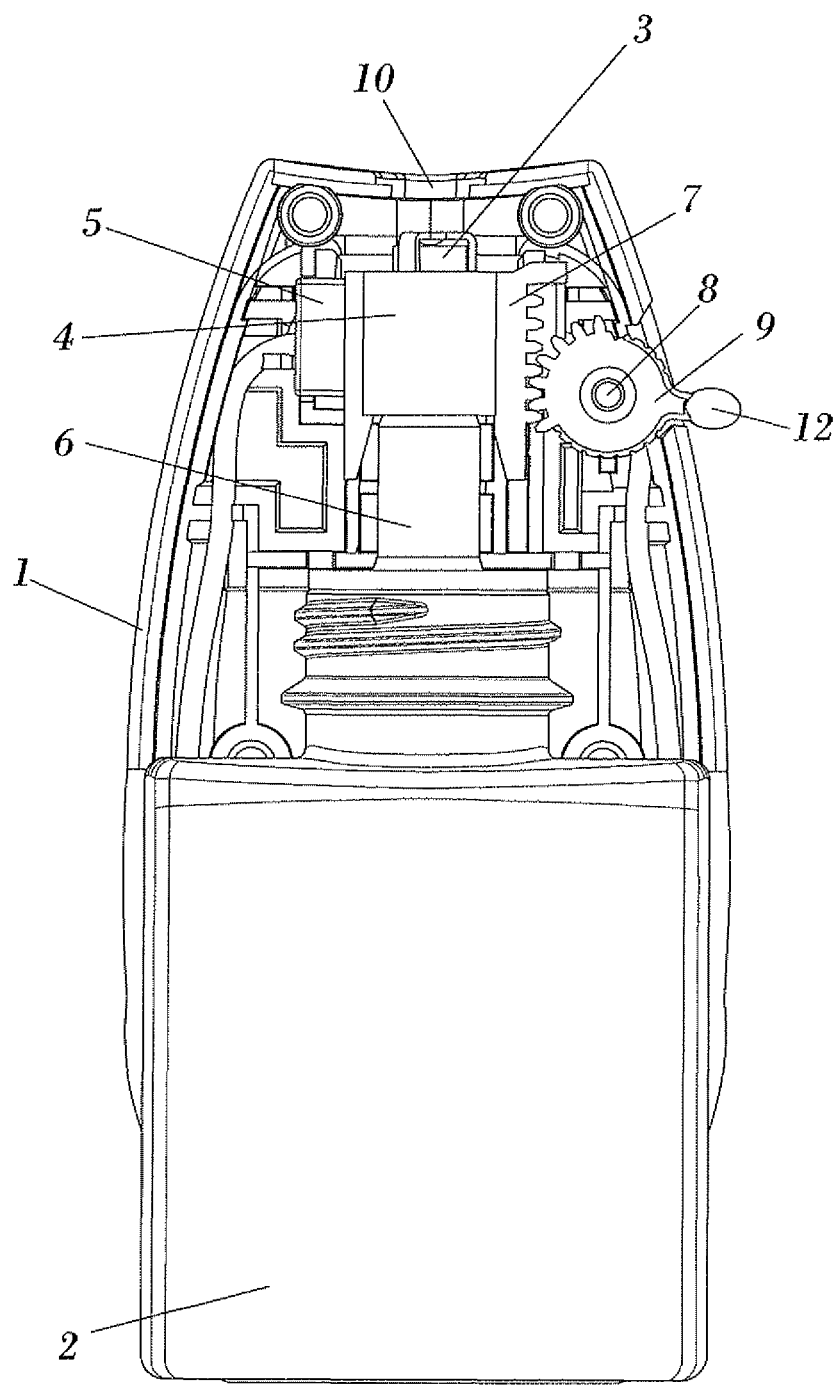
FIG. 2.—shows a similar representation than FIG. 1 in which the wick is provided with a protective sleeve. The figure shows the device in the minimum evaporation position, during a normal use of the device when it is plugged in an electric outlet of a wall.
Figure 3:
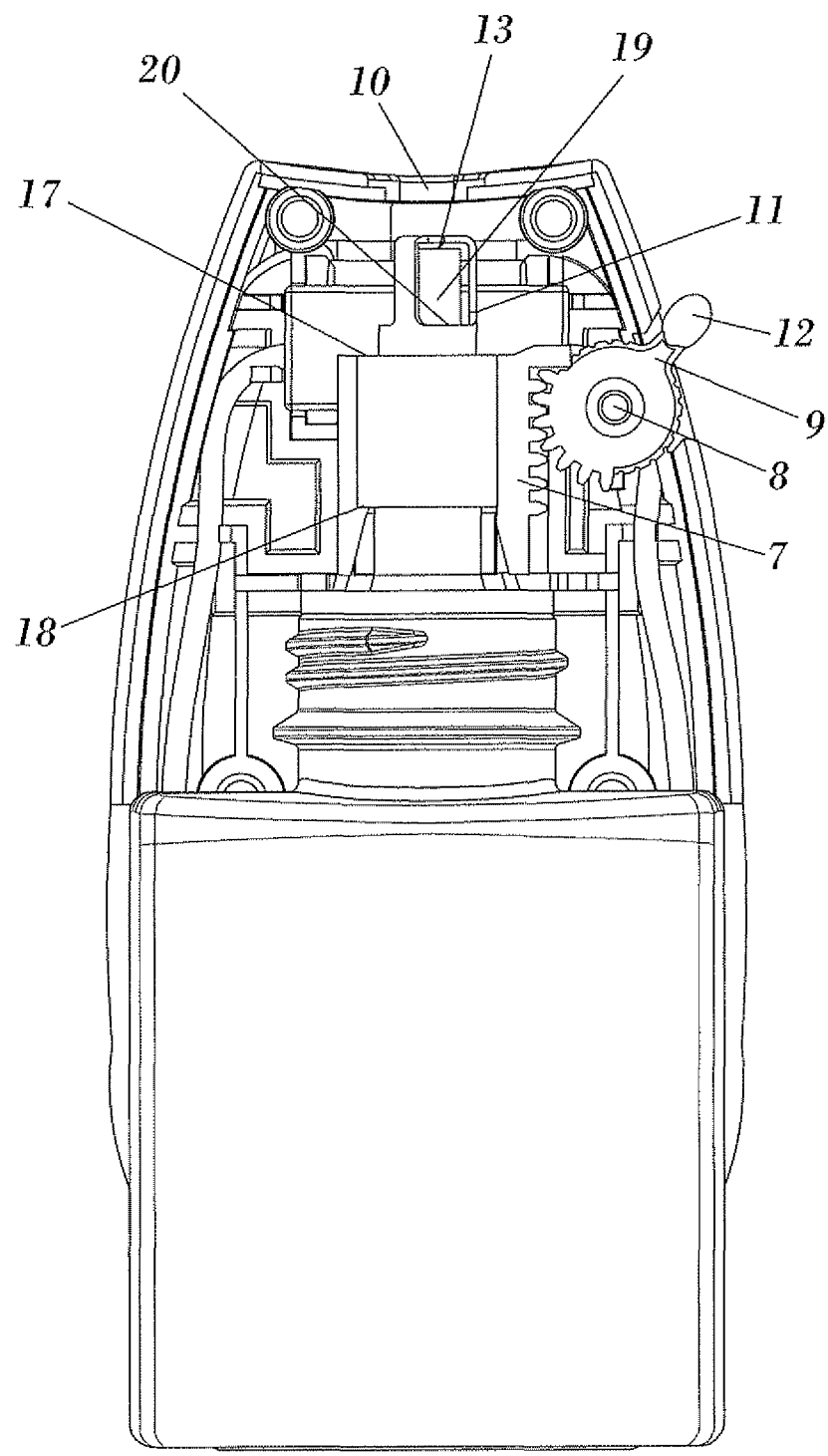
FIG. 3,—is a representation similar to FIG. 2, in which the device is in the maximum evaporation position.
Figure 4:
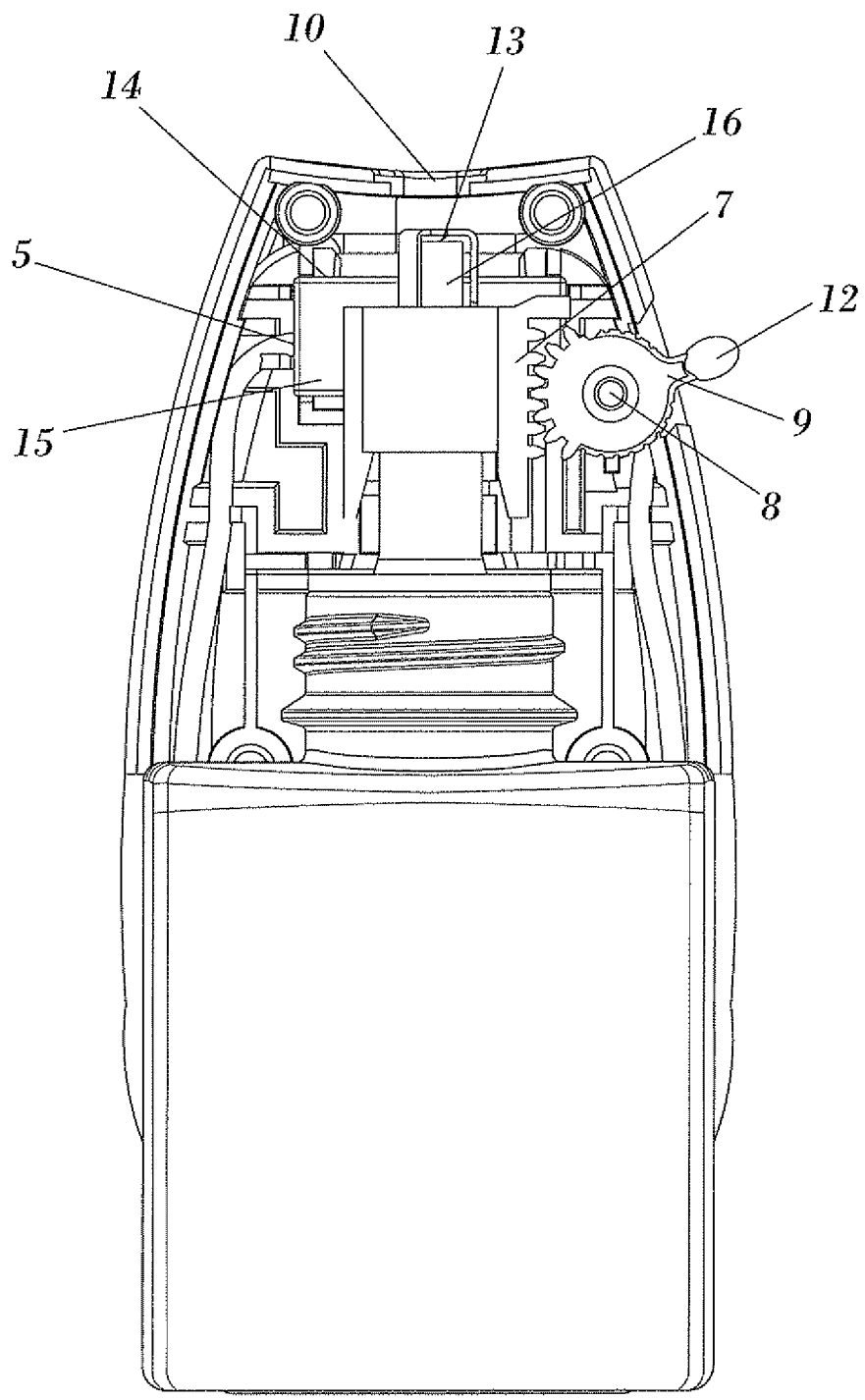
FIG. 4.—is a representation similar to FIG. 2, in which the device is in an intermediate evaporation position.

In the preferred embodiment of FIGS. 2 to 4, a sleeve (6) is tightly covering the part of the wick protruding from the container except for the upper end (19) of the same which is open to the air. This upper end (19) of the wick open to the air, extends from the top (20) of the sleeve (6) and the upper base (13) of the wick.

This sleeve (6) serves to protect and retain the wick in a desired straight position and contributes to thermally isolate the wick from the heat generated by an electric heater, except for said upper end (19) of the wick.

The inner diameter of the shield member (4) is slightly larger than the outer diameter of the sleeve (6) as it can be appreciated for example in FIG. 5.

In the embodiment of FIG. 1 in which the wick is not provided with that sleeve (6), the shield member (4) itself around the wick also serves to some extend to avoid undesired bending of the wick.

In the minimum evaporation position shown in FIGS. 2 and 5, a major part of the shield member (4) is interposed between said resistor (5) and said upper end (19) of the wick, so that the temperature at the upper part of the wick is minimum and the degree of evaporation of the volatile substance in this configuration of the device is also minimum. In this minimum evaporation position, a major part of the shield member is positioned at the same level, that is at the same high, than the resistor (5) in an operational position of the device.

In the maximum evaporation position shown in FIG. 3, a major part of the shield member (4) is located below said resistor (5), so that a major part of the shield member is not interposed between the resistor and the wick, thus the temperature at the upper part of the wick is maximum.

In this preferred embodiment of the invention, the shield member (4) is configured as a tubular body, preferably a tubular cylinder, having open upper and lower bases (17,18), and it is arranged in such a manner that the wick (4) is located inside said tubular cylinder. The shield member is supported by said casing, so that it can move vertically in a guided manner and coaxially with respect to the wick.

As shown in FIG. 2, in the minimum evaporation position, the upper base (17) of the shield, is located at a lower level than the upper base (13) of the wick, and slightly above the upper surface (14) of the resistor.

In turn, a part of the resistor (5) is located above or at a higher level than the top edge (20) of the sleeve (6), so that a part of the resistor is facing directly the upper end (19) of the wick, or in other words a part of the resistor is at the same level than the upper end (19) of the wick.

The height of the tubular sleeve (4) is similar or slightly larger than the height of the resistor (5).

Alternatively, the shield member (4) may comprise a planar wail or a C-shaped wall, also arranged between the resistor and the wick, and being vertically displaceable in a direction parallel to the axis of the wick.

The device includes a mechanism for moving the shield member up and down for regulating the degree of evaporation. In this preferred embodiment, this mechanism comprises a gear wheel (9) rotatably mounted about a shaft (8) fixed to the casing (1), and a toothed rack (7) provided on a side surface of the shield member, wherein the gear wheel and the toothed rack are meshed so that rotation of the gear wheel causes the vertical displacement of the shield member (4) to cover or uncover the wick progressively.

The gear wheel (9) is accessible from the outside of the casing by means of a knob (12), so that the user can move the shield member up and down by actuating in that knob, and set shield member at any desired intermediate fixed position between the maximum and minimum end positions.

An opening (10) is provided at the upper part of the casing (1) for the passage and diffusion of the evaporated substance to the exterior of the device, for that this opening (10) is located over the upper end (13) of the wick.

Since the shield member (4) is displaceable from the level of the resistor towards the bottom of the device, there is no need to have a large space between the upper end of the wick and the opening (10). As it can be appreciated in the attached figures, the upper end of the wick (13) can be arranged very close to the opening (10) compared with the air-fresheners of the state of the art, so that the risk of having part of the vapor dispersed and condensate inside the casing is significantly reduced.

Further preferred embodiments of the invention are described in the dependent claims.

The invention claimed is:

1. Electric device for evaporation of volatile substances comprising:
    a casing;
    a container of volatile substances engaged with said casing, wherein said container is provided with a wick having an upper part protruding from said container, and a lower part inside said container;
the device further comprising
    heating means arranged in said casing for heating said upper part (11) of the wick; and
    means for regulating a degree of evaporation of said volatile substance,
    said means for regulating the degree of evaporation of the volatile substance comprises a shield member which is displaceable between a minimum evaporation position in which part of the shield member is interposed between said heating means and said upper part of the wick, so that a temperature at the upper part of the wick is minimum, and a maximum evaporation position in which part of the shield member is located below said heating means, so that the temperature at the upper part of the wick is maximum.

2. Device according to claim 1, wherein the shield member is displaceable in a direction substantially parallel to an axis of the wick.

3. Device according to claim 1, wherein said heating means comprises one heating resistor which is facing a side surface of the wick.

4. Device according to claim 1, wherein the heating resistor is located at a lower level than an upper base of the wick.

5. Device according to claim 1, wherein said shield member is a tubular cylinder supported by said casing, and wherein the wick is located inside said tubular cylinder.

6. Device according to claim 1, further comprising a gear wheel rotatably mounted about a shaft fixed to said casing, and a toothed rack provided in said shield member meshed with said gear wheel, so that the shield member is displaceable by means of said gear wheel.

7. Device according to claim 1, further comprising a protective sleeve tightly covering a part of the wick protruding from the container, except for the upper end of the wick.

8. Device according to claim 7 wherein in the maximum evaporation position, a part of the resistor is facing said upper end of the wick.

9. Device according to claim 1, wherein the upper part of the casing is provided with an opening located over the upper end of the wick for exit of the vaporized substance.

10. Device according to claim 1, wherein said heating resistor is a rectangular prismatic body.

* * * * *